United States Patent [19]

Nara et al.

[11] 4,045,298

[45] Aug. 30, 1977

[54] ANTIBIOTIC XK-62-2 AND PROCESS FOR PRODUCTION THEREOF

[75] Inventors: Takashi Nara, Tokyo; Seigo Takasawa, Kawasaki; Ryo Okachi, Machida; Isao Kawamoto, Machida; Mitsuyoshi Yamamoto, Machida; Seiji Sato, Machida; Tomoyasu Sato, Machida; Atsuko Morikawa, Tama, all of Japan

[73] Assignee: Abbott Laboratories, North Chicago, Ill.

[21] Appl. No.: 696,306

[22] Filed: June 15, 1976

Related U.S. Application Data

[62] Division of Ser. No. 364,058, May 25, 1973.

[30] Foreign Application Priority Data

May 27, 1972 Japan .................................. 47-52177
Sept. 11, 1972 Japan .................................. 47-90477

[51] Int. Cl.$^2$ .............................................. C12D 9/14
[52] U.S. Cl. .................................. 195/80 R; 536/17; 195/96
[58] Field of Search .......................... 195/80 R, 81

[56] References Cited

PUBLICATIONS

Kershner; Separation, Structural and Physical Studies on the Gentamicin C Complex; Rutgers, The State University of New Jersey; 1971.

*Primary Examiner*—Lionel M. Shapiro
*Assistant Examiner*—Robert J. Warden
*Attorney, Agent, or Firm*—Fitzpatrick, Cella, Harper & Scinto

[57] ABSTRACT

The antibiotic XK-62-2 is produced by fermentation of microorganisms belonging to the genus Micromonospora. The antibiotic is accumulated in the culture liquor and is isolated therefrom.

12 Claims, 3 Drawing Figures

NUCLEAR MAGNETIC RESONANCE SPECTRUM
OF THE SULFATE OF XK-62-2

ANTIBIOTIC XK-62-2 AND PROCESS FOR PRODUCTION THEREOF

This is a division, of application Ser. No. 364,058, filed May 25, 1973.

BACKGROUND

The present invention relates to a new antibiotic, identified as XK-62-2, and a process for producing the same. More particularly, the present invention relates to a process which comprises culturing an antibiotic XK-62-2 producing microorganism belonging to the genus Micromonospora in a suitable medium to form a novel antibiotic XK-62-2, and recovering the antibiotic from the culture liquor.

The new antibiotic XK-62-2 is a water-soluble, basic antibiotic which has very strong antibacterial activity both in vitro and in vivo against various Gram-positive and Gram-negative bacteria. It also possesses strong antibacterial activity against certain strains of *Staphylococcus aureus* and *Escherichia coli* which are resistant to various known antibiotics. Moreover, the present antibiotic is very effective upon the microorganisms of the genus Proteus and Pseudomonas upon which very few antibiotics have been known to be effective; and of the microorganisms of the genus Pseudomonas, the present antibiotic is especially effective upon the strains which are resistant to antibiotic gentamicin $C_{1a}$. (Cooper et al: Journal of Chemical Society 1971, p, 3126–3129).

It has been found that XK-62-2 exhibits very excellent therapeutic effect upon various infections (of human beings and animals) caused by the above-described various pathogenic bacteria. In view of this excellent antibacterial activity, XK-62-2 may be used for medicinal purposes as an antibiotic. It may also be used as an additive for animal feed as a growth promoter.

Due to its nature, which will be more fully described hereinafter, it is believed that the new antibiotic belongs to the gentamicin complex.

The production of the basic antibiotic, gentamicin is disclosed in U.S. Pat. No. 3,091,572. Thus, it is known that gentamicin as well as two additional fractions, identified as fraction A and fraction B, may be produced by microorganisms belonging to the species, *Micromonospora echinospora* and *Micromonospora purpurea*. Additional researchers have determined that the gentamicin complex contains an additional six components. "Separation, Structural and Physical Studies on the Gentamicin C Complex," Kershner, Rutgers, the State University of New Jersey, 1971. These six components are designated as: $C_1$, $C_{2a}$, $C_2$-I, $C_2$-II, $C_2$-III, and $C_{1a}$.

The antibiotic of the present invention is most closely related to the fraction $C_{2a}$, but due to significant differences in Nuclear Magnetic Resonance spectra, as will also be more fully described hereinafter, the antibiotic of the present invention is considered different from the fraction $C_{2a}$, as reported in the known art.

SUMMARY OF THE INVENTION

According to the present invention, the antibiotic XK-62-2 is produced by fermenting microorganisms belonging to the genus Micromonospora in a suitable nutrient medium and thereafter isolating the specific antibiotic. In this respect, the present inventors have isolated several new strains belonging to a new species of the genus Micromonospora which readily produce the antibiotic. The type culture has been named *Micromonospora sagamiensis MK*-65; and two varieties which have also been identified have been named *Micromonospora sagamiensis* var. *nonreducans* MK-62, and *Micromonospora sagamiensis* var. *flava* Mm-628. These three strains have been deposited with the American Type Culture Collection, Rockville, Maryland and have been accorded accession numbers 21826, 21803 and 21827 respectively. The strains have the following properties:

I. Morphology:

Well developed, branching, non-septate substrate mycelia having a diameter of about $0.5\mu$ are formed but no true aerial mycelium is formed. Spores are formed very well and single spores are produced at the ends of simple sporophores ($1.0 - 2.0\mu$ in length) branched from the substrate mycelia. Many spores are formed around the ends of the substrate mycelia. Matured spores have a diameter of about $1.0\mu$ and are oval of spherical in shape with a rough surface. II. Cultural characteristics on various media:

The MK-65 strain: Growth is brown on well-growing agar media forming many spores but is orange on poor-growing media on which spores are rather poorly formed. Sometimes the color tone varies depending upon the media.

The Mm-628 strain: Growth is very poor on ordinary synthetic media and grows well only on natural media forming a spore layer. The color tone is clearly different from that of the MK-65 strain on all media, showing mustart color to light wheat. When matured, growth is brownish to blackish due to the color of the spores, and sometimes grayish.

The MK-62 strain: Generally, many spores are produced on well-growing agar media on which growth is mostly dark brown. However, growth is orange on poor-growing media and spores are not readily formed. Further, a black spore layer is formed on agar media on which the growth of the substrate mycelia is poor but spores are readily formed. In liquid media, growth is orange due to the color of the substrate mycelia.

Cultural characteristics on various media after culturing at 27° C for 2 weeks are shown in Table 1. The color indications are given according to the classifications in Color Harmony Manual (Container Corporation of America).

TABLE 1

| Medium | Strains | Micromonospora sagamiensis var. nonreducans MK-62 | Micromonospora sagamiensis MK-65 | Micromonospora sagamiensis var. flava Mm-628 |
|---|---|---|---|---|
| Czapek's agar | | G: moderate, flat<br>S: bright melon yellow (3 ia)<br>to dark brown (3 pn)<br>SP: none | G: moderate, flat<br>S: apricot (4 ga)<br>to dark brown (4 nl)<br>SP: none | G: poor |
| Glucose: asparagine agar | | G: moderate, flat<br>S: brick red henna (5 ng)<br>SP: none | G: poor to moderate, flat<br>S: tile red (5 ne)<br>SP: none | G: poor |
| Nutrient agar | | G: poor to moderate, flat<br>S: orange (4 la)<br>SP: none | G: poor to moderate, flat<br>S: light gold (2 ic)<br>SP: none | G: poor to moderate, flat<br>S: light wheat (2 ea)<br>SP: none |

TABLE 1-continued

| Medium | Strains | Micromonospora sagamiensis var. nonreducans MK-62 | Micromonospora sagamiensis MK-65 | Micromonospora sagamiensis var. flava Mm-628 |
|---|---|---|---|---|
| Egg albumin agar | | G: poor, flat black spore layer | G: poor to moderate, flat S: cocoa brown (5 lg) SP: none | G: poor |
| Starch agar | | G: moderate, granular S: light copper brown (5 pg) SP: none | G: moderate, granular S: deep brown (4 pl) SP: none | G: poor |
| Malt extract-yeast extract agar | | G: moderate, raised S: deep brown (5 pl) SP: none | G: moderate, granular S: chestnet brown (4 ni) | G: good, raised, ridged S: mustard brown (2 pl) to black SP: none |
| Oat meal agar | | G: poor, flat S: orange (4 la) | G: poor, flat S: orange (4 la) | G: poor S: mustard brown (2 pl) to black |
| | | SP: none | SP: none | SP: none |
| Dextrose-NZ amine (1:3) agar | | G: moderate, raised S: luggage tan (4 ne) SP: none | G: moderate, flat S: bright yellow (3 la) SP: none | G: poor, granular S: light wheat (2 ea) SP: none |
| Bennett's agar | | G: moderate, raised, ridged S: dusty orange (4 lc) SP: none | G: moderate, granular S: oak brown (4 pi) SP: none | G: moderate, flat S: mustard brown (2 pi) SP: none |
| Emerson's agar | | G: poor, plicate S: bright orange (4 na) SP: none | G: poor to moderate, granular S: orange (4 la) SP: none | G: moderate, granular S: bright melon yellow (3 ia) SP: none |
| Glucose-yeast extract agar | | G: moderate, raised S: bright orange (4 na) SP: none | G: moderate, granular S: russet orange (4 nc) SP: none | G: moderate, granular S: mustard brown (2 pi) SP: none |
| Tyrosine agar | | G: moderate, flat SP: none | G: poor SP: none | G: poor SP: none |

G: growth;
S: color of substrate mycelium;
SP: soluble pigment

III. Physiological Properties:

Physiological properties of the MK-62, MK-65 and Mm-628 strains are shown in Table 2. The optimum temperature is determined after 5 days of culturing and the action upon milk and the decomposition of cellulose are observed after one month of culturing. The other observations are based on culturing at 27° C for 2 to 3 weeks.

TABLE 2

| Physiological properties | Micromonospora sagamiensis var. nonreducans MK-62 | Micromonospora sagamiensis MK-65 | Micromonospora sagamiensis var. flava Mm-628 |
|---|---|---|---|
| liquefaction of gelatin | − | ± | ± |
| liquefaction of milk | − | + (slowly) | + (slowly) |
| coagulation of milk | − | − | − |
| Cellulose decomposition | ± | ± | ± |
| Starch hydrolysis | + | + | + |
| Utilization of carbon sources | | | |
| D-arabinose | − | − | + |
| D-galactose | + + | + | ± |
| D-glucose | + + | + + | + + |
| Glycerol | − | − | − |
| D-lactose | − | − | − |
| Levulose | + + | + | − |
| L-inositol | − | − | − |
| D-mannitol | − | − | − |
| D-raffinose | − | − | − |
| L-rhamnose | − | − | − |
| D-xylose | + + | + + | + + |
| Sucrose | + | + | + |
| Optimum growth pH | 7.0 – 8.0 | 7.0 – 8.0 | 7.0 – 8.5 |
| Optimum growth temperature | 30° C – 40° C | 30° C – 40° C | 30° C – 40° C |
| Nitrate reduction | − | + | − |
| Tyrosinase formation | − | − | − |
| Melanoid formation | − | − | − |

Since the MK-62, MK-65 and Mm-628 strains do not form true aerial mycelia, and form a single spore on substrate mycelia, these strains are regarded to belong to the genus Micromonospora. In view of the differences in color tone, and the surface spore and other differences from the known microorganisms of the genus Micromonospora the MK-62, MK-65 and Mm-628 strains were determined to belong to a new species belonging to the genus Micromonospora.

The MK-65 strain was chosen as the type culture and was named Micromonospora sagamiensis because it was isolated from forest soil in the suburbs of Sagamihara-shi, Kanagawa-ken, Japan. The MK-62 strain has properties very similar to those of the MK-65 strain except for a difference in the reduction of nitric acid, liquefaction and coagulation of milk and color of mycelium on various media. Accordingly, the MK-62 strain was considered as a variant of the type culture and named Micromonospora sagamiensis var. nonreducans because of its failure to reduce nitric acid. The Mm-628 strain, on the other hand, is different from the first two in that the growth is generally poorer and is mustard brown to light wheat on agar medium, and that is utilizes D-arabinose but not levulose. Accordingly, this strain was also considered to be a variant of the type culture and was named Micromonospora sagamiensis var. flava because of its yellow color tone.

In addition to producing the antibiotic XK-62-2, the members of the new species, described above have also been found to produce other antibiotics such as those classified as belonging to the gentamicin C complex. Accordingly, this invention also includes the new process of producing these latter antibiotics.

We have also found that certain other strains belonging to the genus Micromonospora will produce the antibiotic XK-62-2, namely *Micromonospora echinospora* NRRL 2985, ATCC 15837, *Micromonospora echinospora* var. *ferruginea* NRRL 2995, ATCC 15836, *Micromonospora echinospora* var. *pallida* NRRL 2996, ATCC 15838 and *Micromonospora purpurea* NRRL 2953, ATCC 15835. These strains are fully described in U.S. Pat. No. 3,091,572 (Japanese Patent Publication No. 21394/69); and are known to produce the antibiotic gentamicin. However, these strains have not heretofore been recognized to produce the antibiotic of the present invention. The above strains are on deposit in the American Type Culture Collection, Rockville, Maryland.

Mutants having an improved property can be obtained from the microorganisms useful in carrying out the present invention by artifical means such as ultraviolet ray irradiation, $Co^{60}$ irradiation, X-ray irradiation and various mutation-inducing chemicals. For example, the present inventors have derived a mutant from *Micromonospora sagamiensis* var. *nonreducans* MK-62 by nitrosoguanidine treatment and named the mutant *Micromonospora sagamiensis* var. *nonreducans* MK-62-NG-164. As shown in Example 5 below, this mutant characteristically produces XK-62-2. The MK-62-NG-164 strain has also been deposited with the American Type Culture Collection, Rockville, Maryland and has been accorded accession number ATCC 21949.

Generally, conventional methods for culturing microorganisms of the actinomycetes may be employed in the process of the present invention. Various nutrient sources may be employed in the culturing medium. As a carbon source, glucose, starch, mannose, fructose, sucrose, dextrin, molasses, etc., may be used along or in combination. Further, hydrocarbons, alcohols, organic acids, etc., may be used depending upon the ability of utilization possessed by the microorganism. Inorganic and organic nitrogen sources such as ammonium chloride, ammonium sulfate, urea, ammonium nitrate, sodium nitrate, etc., and natural nitrogen sources such as peptone, meat extract, yeast extract, dry yeast, corn steep liquor, soybean powder, casamino acid, soluble vegetable protein, etc., may be used alone or in combination. In addition, such inorganic salts as sodium chloride, potassium chloride, calcium carbonate and phosphate may be added to the medium if necessary. Furthermore, organic or inorganic materials capable of promoting growth of the microorganism may be properly added thereto.

A liquid culturing method, especially a submerged stirring culturing method is most suitable for the present process. The culturing temperature is between 25° and 42° C and it is desirable to carry out culturing at an approximately neutral pH.

The antibiotic of the invention is formed and accumulated in the culture liquor usually after 1 to 12 days of culturing. When the yield of XK-62-2 in the culture liquor reaches a maximum, culturing is discontinued and the desired product is isolated and purified from the culture liquor after the microbial cells have been removed such as by filtration.

Isolation and purification of the antibiotic from the filtrate is carried out according to the methods usually used in the isolation and purification of microbial metabolic products from culture liquor.

Since XK-62-2 is basic and is very soluble in water but poorly soluble in ordinary organic solvents, the desired product can be purified by the methods usually used for the purification of so-called water-soluble bacis antibiotics. More specifically, XK-62-2 may be purified by a proper combination of: adsorption and desorption from cation exchange resin and active carbon; column chromatography using cellulose, Sephadex LH-20 and silica gel; and the like methods. Since the free base of the present substance is soluble in acetone and the sulfate is poorly soluble in methanol, the desired substance can be dissolved and precipitated by properly combining these properties.

For example, the culture filtrate is first adjusted to a pH of 7.5 and then subjected to adsorption on cation exchange resin, Amherlite (trade name) IRC-50 ($NH_4^+$ form). After washing with water elution is carried out with 1N aqueous ammonia. The active fraction is concentrated under reduced pressure. The concentrate is then treated with an anion exchange resin, Dowex (trade name) 1×2 ($OH^-$ form) and further concentrated under reduced pressure. The concentrate is adjusted to a pH of about 10.5 and five volumes of acetone is added thereto. The resultant precipitate is removed by filtration and the filtrate is concentrated and adjusted to a pH of 4.5 with sulfuric acid. To this, 5–10 volumes of methanol is added. The precipitate is recovered by filtration and dried in vacuo. White crude powders are obtained.

The thus obtained crude powders are suspended in the lower layer of a solvent mixture of chloroform, isopropanol and 17% aqueous ammonia (2:1:1); and the resultant suspension is subjected to silica gel column chromatography. Elution is carried out with the same solvent. The fractions of XK-62-2 are collected and concentrated under reduced pressure. After freeze-drying the concentrate, a white free base of the antibiotic is obtained. Otherwise, the concentrate of the active fraction is adjusted to a pH of 4.5 with sulfuric acid and then subjected to filtration. After freeze-drying the filtrate, a white sulfate of XK-62-2 is obtained.

THE ANTIBIOTIC

The free base of the antibiotic XK-62-2 is a white basic powder. An elementary analysis reveals: C = 51.90%, H = 8.81%, N = 15.18% and O = 24.11% (by difference). The melting point of the sulfate is 260° C (decomposition). The specific rotation of the free base is $[\alpha]_D^{20} = +116°$ (C 1, $H_2O$).

610, 1040, 1110, 1285, 1340, 1390, 1460, 1510, 1620, 2050, 2920, 3030, 3350.

Figure 1:
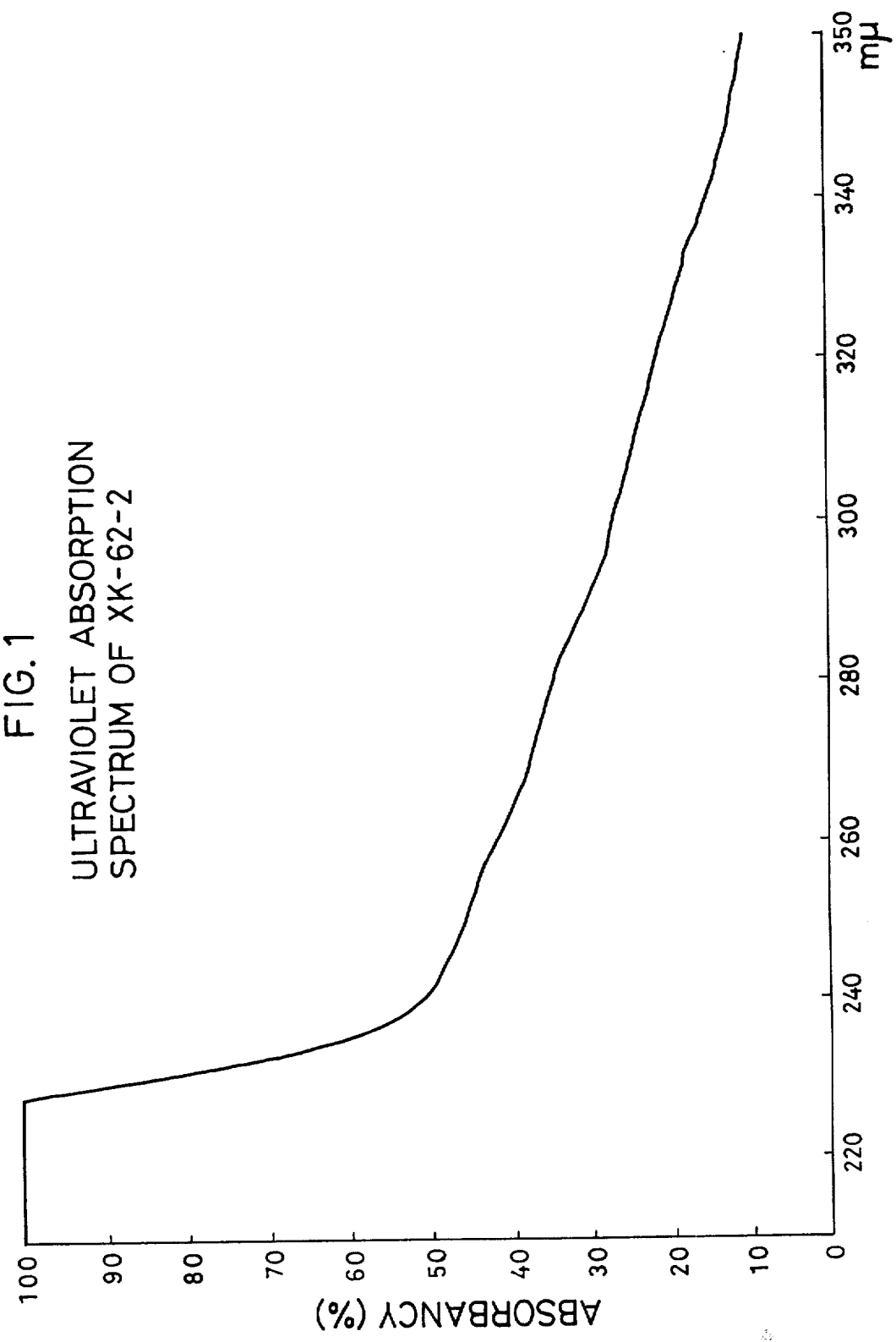
FIG. 1 illustrates the ultraviolet absorption spectrum of an aqueous solution of XK-62-2. This reveals no characteristic absorption maxima between 220–360 mμ, but only shows terminal absorptions.
Figure 2:
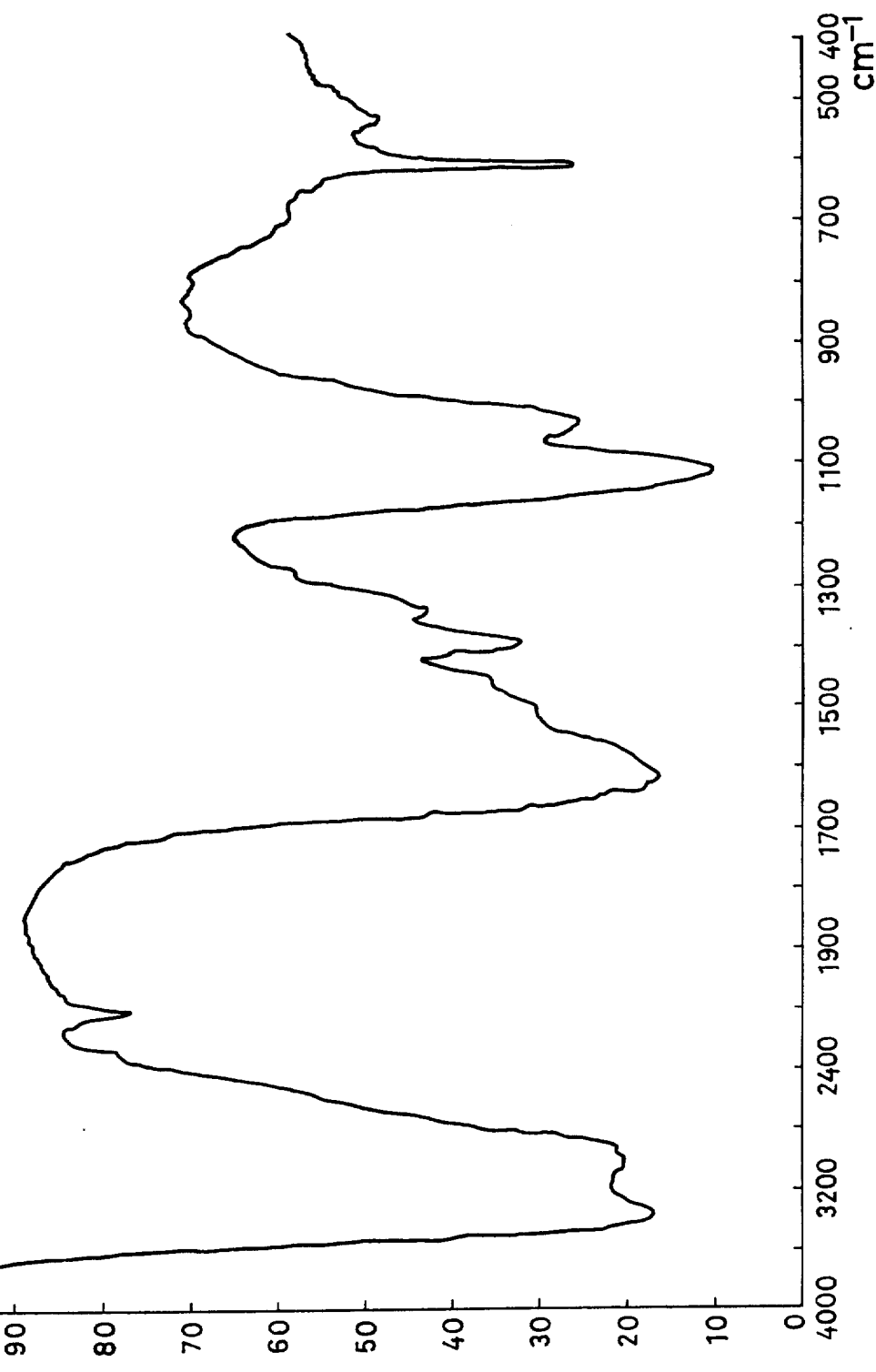
FIG. 2 illustrates the infrared absorption spectrum of the antibiotic (KBr tablet). As is apparent from the figure, XK-62-2 shows peaks at the following wavelengths expressed in reciprocal centimeters.
Figure 3:
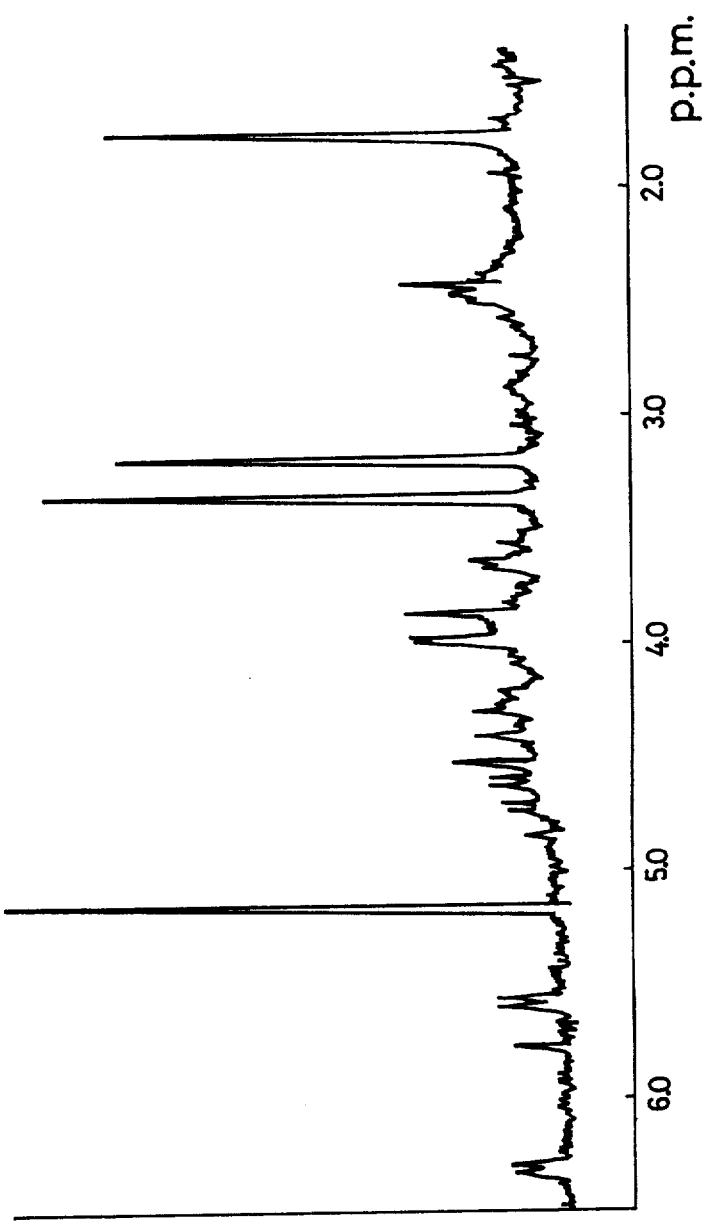

The NMR spectrum of the sulfate of XK-62-2 is illustrated in FIG. 3. The NMR spectrum is measured with a Varian Associates HA-100 spectrometer after the hydrogen atoms of XK-62-2 are replaced with deuteriums by repeated freeze-drying in heavy water. The absorptions at 5.60 ppm and 6.32 ppm are based on the anomeric proton of constituent sugar. The absorptions of N-methyl and tertiary C-methyl groups are confirmed respectively at 3.38 ppm and 1.80 ppm. Characteristically, another absorption of N-methyl group is observed at 3.21 ppm with a difference of 0.17 ppm from 3.38 ppm.

As a result of the measurement of mass spectrum using an apparatus having a high resolving power, it is determined that XK-62-2 has a molecular ion (M +

1)+of 464, therefore, a molecular weight of 463 and a molecular formula of $C_{20}H_{41}N_5O_7$. Consequently, the elementary analytical values as calculated are C = 51.84%, H = 8.86%, N = 15.12% and O = 24.19%.

From the foregoing data, the antibiotic XK-62-2 is believed to have the following structural formula:

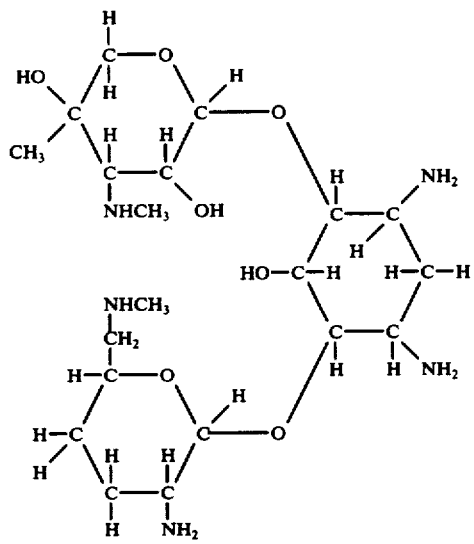

The free base of XK-62-2 is very soluble in water, soluble in methanol, ethanol or acetone but insoluble in such organic solvents as chloroform, benzene, ethyl acetate, butyl acetate, ether, butanol, petroleum ether, n-hexane, etc. The sulfate of XK-62-2 is very soluble in water but insoluble in organic solvents such as methanol, acetone, etc.

The Rf values of XK-62-2 obtained as a result of paper chromatography and thin layer chromatography using various developers are shown in the following Table 3.

TABLE 3

1) Rf values of XK-62-2 by ascending paper chromatography (at 28° C)

| Developer | Rf value | Developing period (hour) |
|---|---|---|
| 20% (W/V) Ammonium chloride | 0.98 | 3 |
| Water-saturated n-butanol | 0.00 | 15 |
| n-Butanol: acetic acid: water ( 3 : 1 : 1 ) | 0.06 | 15 |
| Water-saturated ethyl acetate | 0.00 | 4 |
| Water-saturated n-butanol containing 2% (W/V) p-toluene sulfonic acid and 2% (V/V) of piperidine | 0.03 | 15 |

2) Rf values of XK-62-2 by silica gel thin layer chromotography (at room temperature)

| Developer | Rf value | Developing period (hour) |
|---|---|---|
| The upper layer of a mixture of chloroform, methanol and 17% aqueous ammonia (2:1:1 by volume) | 0.86 | 3 |
| 10% ammonium acetate: methanol (1:1 by volume) | 0.21 | 3 |

The Rf values of XK-62-2 as compared with those of known antibiotics by paper chromatography using a developer of the lower layer of chloroform, methanol and 17% aqueous ammonia (2:1:1) are shown in the following Table 4.

TABLE 4

Ascending paper chromatography (at room temperature)
Developing period : 12 hours

| Antibiotics | Rf value |
|---|---|
| Gentamicin A | 0.00 |
| Gentamicin $C_{1a}$ | 0.18 |
| Gentamicin $C_2$ | 0.38 |
| Gentamicin $C_1$ | 0.59 |
| Antibiotic No. 460 | 0.01 |
| Sisomicin | 0.18 |
| Neomycin A | 0.00 |
| Neomycin B | 0.02 |
| Kanamycin A | 0.01 |
| Kanamycin B | 0.00 |
| Paromomycin | 0.02 |
| Nebramycin complex | 0.02 |
| Tobramycin | 0.00 |
| XK-62-2 | 0.49 |

Based on the above results, the antibiotic of the invention is considered to belong to the gentamicin complex. As discussed hereinabove, the production of the antibiotic gentamicin is disclosed in U.S. Pat. No. 3,091,572. In this patent, the properties and structure of gentamicin as well as two associated fractions identified as fraction A and fraction B are disclosed. Subsequently, additional fractions have been isolated. For example, the thesis by Allan S. Kershner, "Separation, Structural and Physical Studies on The Gentamicin C Complex," Rutgers University, The State University of New Jersey, 1971, discusses a series of gentamicin antibiotics identified as $C_1$, $C_{2a}$, $C_2$-I, $C_2$-II, $C_2$-III and $C_{1a}$.

The antibiotic of the present invention, although closely related to the known antibiotics within the gentamicin complex, is nevertheless determined to be a heretofore unrecognized antibiotic based upon the characteristics described above, particularly the ultraviolet absorption spectrum, infrared absorption spectrum and Nuclear Magnetic Resonance spectrum. More specifically, as stated hereinabove, the antibiotic of the present invention is particularly similar to the gentamicin fraction $C_{2a}$. As reported, this fraction does not have the same Nuclear Magnetic Resonance spectrum as the present antibiotic. Thus, XK-62-2, is considered a novel substance possessing excellent antibiotic properties, as will be illustrated in the following tables.

The antibacterial spectra of XK-62-2 against various microorganisms is shown in the following Table 5.

TABLE 5

Antibacterial spectra of XK-62-2 by agar dilution method

| Microorganisms tested | Minimum inhibitory concentration (γ/ml) |
|---|---|
| *Streptococcus faecalis* ATCC 10541 | 1.05 |
| *Staphylococcus aureus* ATCC 6538P | < 0.0041 |
| *Staphylococcus aureus* KY 8942 (resistant to kanamycin, paromomycin and streptomycin) | 0.065 |
| *Staphylococcus aureus* KY 8950 (resistant to streptomycin, tetracycline, penicillin and sulfonamide) | 0.0082 |
| *Staphylococcus aureus* KY 8953 (resistant to streptomycin, kanamycin, paromomycin, tetracycline, neomycin, kanendomycin and erythromycin) | 0.0041 |
| *Staphylococcus aureus* KY 8956 (resistant to streptomycin, paromomycin, tetracycline, erythromycin and oleandomycin) | < 0.001 |
| *Staphylococcus aureus* KY 8957 (resistant to chloramphenicol, streptomycin, kanendomycin, tetracycline and paromomycin) | 0.0021 |
| *Bacillus subtilis* No. 10707 | < 0.004 |
| *Bacillus cereus* ATCC 9634 | 0.016 |
| *Bacillus cereus* var. *mycoides* ATCC 9463 | 0.0082 |
| *Klebsiella pneumoniae* ATCC 10031 | 0.0082 |
| *Escherichia coli* ATCC 26 | 0.0082 |

TABLE 5-continued

Antibacterial spectra of XK-62-2 by agar dilution method

| Microorganisms tested | Minimum inhibitory concentration (γ/ml) |
|---|---|
| *Escherichia coli* KY 8302 (resistant to chloramphenicol, streptomycin, kanamycin, paromomycin, tetracycline and spectinomycin) | 0.033 |
| *Escherichia coli* KY 8310 (resistant to chloramphenicol, streptomycin, kanamycin, gentamicin, kanendomycin, paromomycin, tetracycline and spectinomycin) | 1.05 |
| *Escherichia coli* KY 8314 (resistant to streptomycin) | 0.0082 |
| *Escherichia coli* KY 8315 (resistant to streptomycin, kanamycin, paromomycin and neomycin) | 0.016 |
| *Pseudomonas aeruginosa* BMH No. 1 | 0.53 |
| *Proteus vulgaris* ATCC 6897 | 0.03 |
| *Shigella sonnei* ATCC 9290 | 0.07 |
| *Salmonella typhosa* ATCC 9992 | 0.018 |

The in vitro activity of XK-62-2 against a variety of Gram-positive and Gram-negative bacteria is far superior to those of streptomycin and kanamycin and the activity is comparable to that of gentamicin. The comparative in vitro activities of these antibiotics against various microorganisms of the genus Proteus are shown in the following Table 6.

The antibacterial activity of XK-62-2 against clinically isolated various strains of *Pseudomonas aeruginosa* is also compared with those of streptomycin, kanamycin, gentamicin complex and gentamicin $C_{1a}$ as is shown in the following Table 7.

In addition, the in vivo activity of XK-62-2 against pathogenic bacterial infections in mice is tested. The mice are infected with an inoculum of $3.8 \times 10^8$ cells/mouse of *Pseudomonas aeruginosa* BMH No. 1 or $6.6 \times 10^7$ cells/mouse of *Pseudomonas aeruginosa* KY 8510 by intraperitoneal injection They are then treated with various doses of the test antibiotic by subcutaneous injection. The effect of XK-62-2 on the protection of the bacterial infections is shown in the following Table 8 wherein ten mice are used in each test.

The in vivo activity of XK-62-2 against pathogenic bacterial infections in mice is further tested using various Gram-positive and Gram-negative bacteria. The mice are infected with an inoculum of the bacteria by intraperitonial injection and then treated with the test antibiotic by subcutaneous injection. The results are shown in the following Table 9.

TABLE 6

| | Minimum inhibitory concentration (γ/ml : by agar dilution method) | | | |
|---|---|---|---|---|
| Microorganisms | XK-62-2 | gentamicin complex | streptomycin | kanamycin |
| *Proteus vulgaris* KY 4296 | 0.021 | 0.021 | — | — |
| *Proteus vulgaris* KY 4297 | 0.021 | 0.021 | — | — |
| *Proteus vulgaris* ATCC 6897 | 0.04 | 0.04 | >40 | 0.34 |
| *Proteus vulgaris* Abbott JJ | 0.021 | 0.021 | >40 | 0.16 |
| *Proteus mirabilis* Finland 9 | 0.04 | 0.04 | >40 | 0.04 |
| *Proteus mirabilis* No. 825 | 0.021 | 0.021 | >40 | 0.04 |
| *Proteus mirabilis* No. 39 | 0.021 | 0.04 | >40 | 0.33 |
| *Proteus morganii* Jenkins | 0.04 | 0.04 | >40 | 0.16 |
| *Proteus rettgeri* Booth | 0.021 | 0.021 | >40 | 0.08 |
| *Proteus rettgeri* Hambrook | 0.021 | <0.01 | >40 | 0.08 |

TABLE 7

| | Minimum inhibitory concentration (γ/ml : by agar dilution method) | | | | |
|---|---|---|---|---|---|
| Strains of *Pseudomonas aeruginosa* | XK-62-2 | gentamicin complex | gentamicin $C_{1a}$ | streptomycin | kanamycin |
| KY 4276 | 0.33 | 0.33 | 0.33 | 2.6 | 1.63 |
| KY 8510 | 0.33 | 1.3 | 2.6 | 0.65 | 13 |
| KY 8511 | >42 | 42 | 42 | >2500 | 13 |
| KY 8512 | 0.33 | 0.65 | 0.33 | 42 | 3.3 |
| KY 8514 | 0.55 | 1.3 | 0.33 | 156 | 208 |
| KY 8515 | >42 | 62 | >42 | 624 | 416 |
| KY 8516 | 0.33 | 1.3 | 5.2 | 0.65 | 26 |
| KY 8520 | 0.33 | 0.65 | 0.33 | 5.2 | 104 |
| KY 8562 | >42 | 62 | >42 | 156 | 167 |

TABLE 8

| | *Pseudomonas aeruginosa* BMH No. 1 | | *pseudomonas aeruginosa* KY 8510 | | |
|---|---|---|---|---|---|
| Dose (mg/ mouse) | XK-62-2 | gentamicin complex | XK-62-2 | gentamicin complex | gentamicin $C_{1a}$ |
| | Survival of mice (%) | | | | |
| 2 | 100 | 100 | 100 | 90 | 20 |
| 1 | 90 | 100 | 80 | 40 | 10 |
| 0.5 | 50 | 70 | 50 | 30 | 0 |
| 0.25 | 10 | 20 | 30 | 10 | 0 |
| 0.125 | 0 | 0 | 0 | 0 | 0 |

TABLE 9

| Organism | challenge inoculum (cells/mouse) | Median effective dose [$ED_{50}$ (mg/kg)] | | Ratio XK-62-2/ gentamicin complex |
|---|---|---|---|---|
| | | XK-62-2 | gentamicin complex | |
| *Staphylococcus aureus* Smith | $1.8 \times 10^6$ | 0.28±0.04 | 0.21±0.05 | 1.33 |
| *Streptococcus pyogenes* $S_{23}$ | $2.7 \times 10^7$ | 17.7±4.8 | 11.8±3.4 | 1.50 |
| *Diplococcus pneumoniae* III | $4.4 \times 10^3$ | 6.6±1.9 | 7.7±1.6 | 0.86 |
| *Escherichia coli* GN 2411-5 | $3.6 \times 10^6$ | 10.8±4.1 | 10.7±2.9 | 1.01 |

TABLE 9-continued

| Organism | challenge inoculum (cells/mouse) | Median effective dose [$ED_{50}$ (mg/kg)] | | Ratio XK-62-2/ gentamicin complex |
|---|---|---|---|---|
| | | XK-62-2 | gentamicin complex | |
| Klebsiella pneumoniae No. 8045 | $1.4 \times 10^8$ | 5.7±1.4 | 7.7±0.9 | 0.74 |
| Proteus mirabilis 1287 | $1.8 \times 10^8$ | 10.4±4.4 | 10.7±3.5 | 0.97 |

As is apparent from the foregoing, XK-62-2 has a very strong antibacterial activity both in vitro and in vivo against a broad range of Gram-positive and Gram-negative bacteria. XK-62-2 also has a strong antibacterial activity against certin strains of Staphylococcus aureus and Eexherichia coli which are resistant to various known antibiotics, and is particularly effective upon the microorganisms of the genera Proteus and Pseudomonas upon which only a few antibiotics have been known to be effective.

From the above Tables, it is demonstrated that XK-62-2 exhibits excellent antibacterial activity and therapeutic effect against certain strains (clinical isolates) of Pseudomonas aeruginosa as compared to those of the gentamicin complex or gentamicin $C_{1a}$ which is one of the components of the gentamicin complex. More specifically, XK-62-2 shows much higher antibacterial activity against Pseudomonas aeruginosa KY 8510 and KY 8516 than the gentamicin complex or gentamicin $C_{1a}$. As a result of enzymological studies it has been found that the KY 8510 and 8516 strains have a specific enzyme system which inactivates gentamicin $C_{1a}$ or kanamycin by acetylating the 6'-$NH_2$ of purpurosamine of gentamicin $C_{1a}$ or the 6'-$NH_2$ of kanamycin. This is the primary reason why the KY 8510 and 8516 strains are resistant particularly to gentamicin $C_{1a}$. However, these two strains are sensitive to XK-62-2. It is considered that this is because XK-62-2 is free from acetylation by this inactivating enzyme since the 6'-$NH_2$ of XK-62-2 is methylated. Thus, as compared to gentamicin $C_{1a}$ or the gentamicin complex which contains gentamicin $C_{1a}$, XK-62-2 is particularly effective in the antibacterial activity against the microorganisms of Pseudomonas aeruginosa, Escherichia coli and Kl bsiella pneumoniae which have this acetylating resistance mechanism.

Other antibiotics, namely, the gentamicin complex [M. J. Weinstein et al: Antimicrobial Agents and Chemotherapy (1963) I and D. J. Cooper et al: J. Infect. Dis. 119, 342 (1969)], antibiotic No. 460 (Japanese Patent Publication 16153/71) and sisomicin [M. J. Weinstein et al: J. Antibiotics 23, 551, 555, 559 (1970)] are water-soluble, basic antibiotics which have a broad range of anti-microbial spectra and are produced by microorganisms of the genus Micromonospora. However, as is clearly evident from the foregoing, XK-62-2 can be clearly distinguished from any of gentamicin A, $C_{1a}$, $C_2$ and $C_1$, each a component of gentamicin complex, antibiotic No. 460 and sisomicin in the Rf values according to paper chromatography. Water-soluble, basic aminoglucosida antibiotics, for example, nebmycin A, neomycin B, kanamycin A, kanamycin B, paromomycin, nebramycin complex and tobramycin, are considered to have similar properties to those of XK-62-2. However, it is also clear that XK-62-2 is completely different from these antibiotics in Rf values.

Practice of certain specific embodiments of the invention is illustrated by the following representative examples.

EXAMPLE 1

A. Culturing of MK-65:

In this example, Micromonospora sagamiensis MK-65 ATCC 21826 (FERM-P No. 1530) is used as the seed strain. One loopful of the seed strain is inoculated into 30 ml of a first seed medium in a 250 ml-Erlenmeyer flask. The first seed medium has the following composition:

| Dextrin | 1% |
|---|---|
| Glucose | 1% |
| Peptone | 0.5% |
| Yeast extract | 0.5% |
| $CaCO_3$ | 0.1% |
| (pH: 7.2 before sterilization) | |

Culturing is carried out with shaking at 30° C for 5 days. Thirty ml of the seed culture is then inoculated into 300 ml of a second seed medium, of the same composition as the first seed medium, in a 2 l-Erlenmeyer flask provided with baffles. The second seed culturing is carried out with shaking at 30° C for 2 days. Then 1.5 l of the second seed culture (corresponding to the content of 5 flasks) is inoculated into 15 l of a third seed medium of the same composition as set forth above, in a 30 l-glass jar fermenter. Culturing in the jar fermenter is carried out with aeration (15 l/min.) and stirring (350 r.p.m.) at 30° C for 2 days. Then, 15 l of the third seed culture is inoculated into 60 l of a fourth seed medium of the same composition as set forth above, in a 300 l-fermenter. Culturing in the fermenter is carried out with aeration (60 l/min.) and stirring (150 r.p.m.) at 30° C for 2 days. Finally, 60 l of the fourth seed culture is inoculated into 600 l of a fermentation medium having the following composition in a 1000 l-fermenter.

| Dextrin | 5% |
|---|---|
| Soybean meal | 4% |
| $CaCO_3$ | 0.7% |
| (pH: 7.2 before sterilization) | |

Culturing in the fermenter is carried out with aeration (600 l/min.) and stirring (150 r.p.m.) at 35° C for 5 days.

B. Isolation of crude antibiotic:

After the completion of fermentation, the culture liquor is adjusted to a pH of 2.0 with 12N sulfuric acid and stirred for 30 minutes. Then, about 10 kg of a filter aid, Radiolite No. 600 (product of Showa Kagaku Kogyo Co., Ltd., Japan) is added thereto and the microbial cells are removed by filtration. The filtrate is adjusted to a pH of 8.0 with 6N sodium hydroxide and passed through a column packed with about 50 l of a cation exchange resin, Amberlite IRC-50 (ammonia form). The active substance is adsorbed on the resin and the eluate is discarded. After washing the resin with water, the active substance is eluted out with 1N aqueous ammonia. The eluate is obtained in fractions and the activity of each of the fractions is determined against *Bacillus subtilis* No. 10707 by a paper disk method using an agar plate.

Active fractions are combined and concentrated in vacuo to about 5 l. The concentrate is then adjusted to a pH of 8.0 with 6N sulfuric acid and passed through a column packed with 1 l of an anion exchange resin, Dowex 1×2 (OH⁻ form). The column is washed with about 5 l of water and the effluent and the washings containing active substance are combined and are concentrated to 1/15 by volume. The concentrate is adjusted to a pH of 10.5 with 6N sodium hydroxide and 5 volumes of acetone is added thereto. The resultant precipitate is removed by filtration and the filtrate is concentrated to 500 ml. The concentrate is adjusted to a pH of 4.5 with 6N sulfuric acid and 2.5 l of methanol is added thereto. After cooling, a white precipitate is obtained. The precipitate is separated by filtration and washed with methanol. After drying in vacuo, about 300 g of white powder is obtained. The white powder is a mixture of the sulfate of gentamicin $C_{1a}$ and the sulfate of XK-62-2, and exhibits an activity of 620 unit/mg (the activity of 1 mg of pure product corresponds to 1000 units).

C. Isolation and purification of XK-62-2:

100 g of the white powder obtained in the above step B are placed to form a thin, uniform layer on the upper part of a 5 cm$\phi$ × 150 cm column packed with about 3 kg of silica gel advancely suspended in a solvent of chloroform, isopropanol and 17% aqueous ammonia (2:1:1 by volume). Thereafter, elution is carried out with the same solvent at a flow rate of about 250 ml/hour. The eluate is separated in 100 ml portions. The active fraction is subjected to paper chromatography to examine the components eluted. XK-62-2 is eluted in fraction Nos. 53-75 and gentamicin $C_{1a}$ is eluted in fraction Nos. 85-120. The fraction Nos. 53-75 are combined and concentrated under reduced pressure to sufficiently remove the solvent. The concentrate is then dissolved in a small amount of water. After freeze-drying the solution, about 38 g of a purified preparate of XK-62-2 (free base) is obtained. The preparate has an activity of 950 unit/mg. Likewise, fraction Nos. 85-120 are combined and concentrated under reduced pressure to sufficiently remove the solvent. The concentrate is then dissolved in a small amount of water. After freeze-drying the solution, about 50 g of a purified preparate of gentamicin $C_{1a}$ (free base) is obtained. The activity of the preparate is about 980 unit/mg.

EXAMPLE 2

In this example, *Micromonospora sagamiensis* var. *flava* Mm-628 ATCC 21827 (FERM-P No. 1531) is used as the seed strain. Seed culturing is carried out in the same manner as described in Example 1 using the same seed medium. Sixty liters of the fourth seed culture is inoculated into 600 l of a fermentation medium in a 1000 l-fermenter. The composition of the fermentation medium is as follows:

| | |
|---|---|
| Soluble starch | 4% |
| Corn steep liquor | 1% |
| Soybean meal | 2% |
| $K_2HPO_4$ | 0.05% |
| $MgSO_4 \cdot 7H_2O$ | 0.05% |

| -continued | |
|---|---|
| KCl | 0.03% |
| $CoCl_2 \cdot 2H_2O$ | 0.005% |
| $CaCO_3$ | 0.1% |

Fermentation is carried out with aeration of 600 l/min and stirring at 150 r.p.m. at 30° C for 96 hours. After the completion of fermentation, the crude product is separated from the culture liquor in the same manner as described in Example 1 to obtain four hundred grams of white powder. As the result of paper chromatography, the powder is found to contain gentamicin $C_1$, $C_2$ and $C_{1a}$ in addition to XK-62-2.

The four hundred grams of white powder is then placed on the upper part of a cylindrical glass column packed uniformly with about 8 kg of silica gel, which is advancely suspended in a solvent of chloroform, isopropanol and 17% aqueous ammonia (2:1:1 by volume). After placing the powder on the upper part of the column, elution is carried out with the same solvent system at a speed of about 500 ml/hour. The eluate is separated in 500 ml portions. Each of the fractions is subjected to paper chromatography. As a result, it is found that each of the components is eluted out in the following order: gentamicin $C_1$, XK-62-2, gentamicin $C_2$ and gentamicin $C_{1a}$. The fractions containing the same component are combined and concentrated. The concentrate is dissolved in water and freeze-dried, and the following components are isolated in the free base form.

| Component | Activity (unit/mg) | Yield (g) |
|---|---|---|
| gentamicin $C_1$ | 880 | 150 |
| XK-62-2 | 932 | 60 |
| gentamicin $C_2$ | 925 | 113 |
| gentamicin $C_{1a}$ | 940 | 52 |

EXAMPLE 3

In this example, *Micromonospora sagamiensis* var. *non-reducans* MK-62, ATCC 21803 (FERM-P No. 1477) is used as the seed strain. One loopful of the seed strain is inoculated into 30 ml of a first seed medium in a 250 ml-Erlenmeyer flask. The seed medium comprises:

| | |
|---|---|
| Dextrin | 1% |
| Glucose | 1% |
| Peptone | 0.5% |
| Yeast extract | 0.5% |
| $CaCO_3$ | 0.1% |
| (pH: 7.2 before sterilization) | |

Culturing is carried out with shaking at 30° C for 5 days. Thereafter, 30 ml of the seed culture is inoculated into 300 ml of a second seed medium, of the same composition set forth above, in a 2 l-Erlenmeyer flask provided with baffles. The second seed culturing is carried out with shaking at 30° C for 2 days. Then, 1.5 l of the second seed culture (corresponding to the content of 5 flasks) is inoculated into 15 l of a third seed medium, of the same composition set forth above, in a 30 l-glass jar fermenter.

Culturing in the jar fermenter is carried out with aeration (15 l/min.) and stirring (350 r.p.m.) at 30° C for 2 days. Then, 15 l of the third seed culture is inoculated into 60 l of a fourth seed medium of the same composition set forth above, in a 300 l-fermenter. Culturing in the fermenter is carried out with aeration (60 l/min.)

and d stirring (150 r.p.m.) at 30° C for 2 days. Finally, 60 l of the fourth seed culture is inoculated into 600 l of a fermentation medium of the following composition in a 1000 l-fermenter.

| Dextrin | 5% |
|---|---|
| Soybean meal | 3.5% |
| CaCO$_3$ | 0.7% |
| (pH: 7.2 before sterilization) | |

Culturing in the fermenter is carried out with aeration (500 l/min.) and stirring (150 r.p.m.) at 30° C for 5 days.

After the completion of fermentation, the culture liquor is adjusted to a pH of 2.0 with 12N sulfuric acid and stirred for 30 minutes. Then, about 10 kg of Radiolite No. 600 (trade name) is added thereto and the microbial cells are removed by filtration. The filtrate is adjusted to a pH of 8.0 with 6N sodium hydroxide and passed through a column packed with about 50 l of a cation exchange resin, Amberlite IRC-50 (ammonia form). The eluate is discarded. After washing the resin with water, the active substance is eluted out with 1N aqueous ammonia. The eluate is obtained in fractions and the activity of each of the fractions is determined against *Bacillus subtilis* No. 10707 by a paper disk method using an agar plate.

Active fractions are combined and concentrated in vacuo to about 5 l. The concentrate is adjusted to a pH of 8.0 with 6N sulfuric acid and passed through a column packed with 1 l of an anion exchange resin, Dowex 1x2 (OH$^-$ form), and thereafter, washed with about 5 l of water to remove impurities. The effluent and the washings containing active substance are combined and concentrated to 1/15 by volume. The concentrate is then adjusted to a pH of 10.5 with 6N sodium hydroxide and 5 volumes of acetone is added thereto. The resultant precipitate is removed by filtration and the acetone layer is concentrated to 500 ml. The concentrate is adjusted to a pH of 4.5 with 6N sulfuric acid and 2.5 l of methanol is added thereto. After cooling, a white precipitate is obtained. The precipitate is separated by filtration and washed with methanol. After drying in vacuo, 20 g of white powder is obtained. The white powder is a mixture of the sulfate of gentamicin $C_{1a}$ and that of XK-62-2 and exhibits an activity of 550 unit/mg.

Five grams of the white power is placed to form a thin, uniform layer on the upper part of a 25 mm$\phi$ × 50 cm column packed with about 300 ml of silica gel which is advancely suspended in a solvent of chloroform, isopropanol and 17% aqueous ammonia (2:1:1 by volume). Elution is then carried out with the same solvent at a flow rate of about 30 ml/hour. The eluate is separated in 10 ml portions. The active fraction is subjected to paper chromatography to examine the components eluted. XK-62-2 is eluted in fraction Nos. 53–75 and gentamicin $C_{1a}$ is eluted in fraction Nos. 85–120. Fraction Nos. 53–75 are combined and concentrated under reduced pressure to sufficiently remove the solvent. The concentrate is dissolved in a small amount of water. After freeze-drying the solution, about 900 mg of a purified preparate of XK-62-2 (free base) is obtained. The preparate has an activity of about 950 unit/mg. Likewise, the fraction Nos. 85–120 are combined and concentrated under reduced pressure to sufficiently remove the solvent. The concentrate is dissolved in a small amount of water. After freeze-drying the solution, about 1.8 g of a purified preparate of gentamicin $C_{1a}$ (free base) is obtained. The activity of the preparate is about 980 unit/mg.

EXAMPLE 4

In this example, *Micromonospora sagamiensis* var. *nonreducans* MK-62 (ATCC 21803) is again used as the seed strain. The composition of the seed medium is as follows:

| Soluble starch | 2% |
|---|---|
| NZ-amine type A | 0.5% |
| Yeast extract | 0.5% |
| CaCO$_3$ | 0.1% |

One loopful of the seed culture is inoculated into 300 ml of the seed medium in a 2 l-Erlenmeyer flask. The first seed culturing is carried out with shaking at 30° C for 4 days. Thereafter, the content of three flasks of the first seed culture is inoculated into 15 l of fresh seed medium in a 30 l-jar fermenter. The second seed culturing is carried out with aeration and stirring at 30° C for 2 days. Then, 150 l of the third seed culture is transferred to a 3000 l-tank containing 1500 l of a fermentation medium having the following composition:

| Soluble starch | 4% |
|---|---|
| Corn steep liquor | 1% |
| Soybean meal | 2% |
| K$_2$HPO$_4$ | 0.05% |
| MgSO$_4$·7H$_2$O | 0.05% |
| KCl | 0.03% |
| CoCl$_2$·2H$_2$O | 0.005% |
| CaCO$_3$ | 0.1% |

Fermentation is carrried out with aeration and stirring at 30° C for 4 days. The production of the active substance reaches a maximum after 4 days of fermentation and the activity of the substance is not reduced for some time.

After completion of fermentation, the culture liquor is adjusted to a pH of 2.0 with oxalic acid and stirred for one hour. In such manner, most of the active substance contained in the microbial cells are extracted into the liquid. Then 20 kg of a filter aid, Celite 545 (trade name) is added thereto and the microbial cells and calcium oxalate are removed by filtration. The filtrate is adjusted to a pH of 6.8 with 6N sodium hydroxide and passed through a column packed with about 100 l of a cation exchange resin, Amberlite IRC-50 (sodium form). The column is washed with water. The effluent and the washings contain impurities and substances which are not adsorbed on the resin and which exhibit an activity only upon Gram-positive microorganisms.

Elution is carried out with about 300 l of 2N sulfuric acid and the active components are recovered in the eluate in fractions. The fractions are combined and adjusted to a pH of 7.0 with 2N sodium hydroxide. The resultant solution is concentrated under reduced pressure to 20 l, and the concentrate is adjusted to a pH of 10.5 with 2N sodium hydroxide. Five volumes of acetone is added thereto while stirring which forms a precipitate which is thereafter separated by filtration and washed with acetone. The filtrate and the washings are combined and concentrated under reduced pressure to 1 l. The concentrate is adjusted to a pH of 4.5 with 6N sulfuric acid. Then 5 l of methanol is added thereto while stirring, and the resultant mixture is allowed to stand in a cold room. A white precipitate is thus formed, and this is separated by filtration and washed with methanol. Upon drying the precipitate in vacuo, about 65 g of crude antibiotic is obtained. The crude powder is a mixture of the sulfate of gentamicin $C_{1a}$ and that of XK-62-2 and has an activity of 450 unit/mg.

Then 60 g of the thus obtained crude powder is dissolved in 10 l of water. The solution is adjusted to a pH of 8.0 with 2N sodium hydroxide and passed through a column packed with 3 l of an anion exchange resin, Amberlite IRA-400 (OH⁻form). The column is washed with 10 l of water and the effluent and the washings containing active substance are combined and concentrated to 1 l. The concentrate is adjusted to a pH of 4.5 with 6N sulfuric acid, and 10 l of methanol is added thereto. In such manner, about 50 g of the purified sulfate of an antibiotic is obtained.

About 50 g of the purified antibiotic is placed on the upper part of a 4 cmφ × 100 cm column packed with about 2.8 l of cellulose powders. Elution is carried out gradually with the lower layer of a mixed solvent of chloroform, methanol and 17% aqueous ammonia (2:1:1 by volume). The speed of elution is controlled not to exceed 100 ml/hour. The eluate is separated into 20 ml portions and XK-62-2 and gentamicin $C_{1a}$ are separately eluted in fraction Nos. 62-86 and in fraction Nos. 95-130 respectively. The fractions of each of the components are combined and concentrated under reduced pressure to remove the solvent and thereafter the concentrate is dissolved in a small amount of water. The resultant solution is adjusted to a pH of 4.5 with 2N sulfuric acid. After freeze-drying, 8.7 g of the sulfate of XK-62-2 (792 unit/mg) and 1.8 g of that of gentamicin $C_{1a}$ (787 unit/mg) are obtained each in the form of a white powder.

To prepare the free base, 5 g of the sulfate of XK-62-2 is dissolved in 500 ml of water and passed through a column packed with 70 ml of an anion exchange resin, Dowex 1×2 (OH⁻form). After washing the column with 500 ml of water, the effluent and the washings which exhibit activity are concentrated under reduced pressure to 100 ml. After freeze-drying the concentrate, 3.3 g of a free base of XK-62-2 (900 unit/mg) is obtained.

EXAMPLE 5

In this example, *Micromonospora sagamiensis* var. *nonreducans* KM-62-NG-164 ATCC 21949, a mutant of *Micromonospora sagamiensis* var. *nonreducans* MK-62, is used as the seed strain. Culturing is carried out in the same manner as described in Example 3 to obtain 95 g of a white powder (750 unit/mg) comprising a mixture of the sulfate of gentamicin $C_{1a}$ and that of XK-62-2. Forty-nine grams of a free base of XK-62-2 (975 unit/mg) and 0.95 g of that of gentamicin $C_{1a}$ (980 unit/mg) are obtained from the powder in the same manner as described in the step C of Example 1.

EXAMPLE 6

In this example, *Micromonospora purpurea* ATCC 15835, NRRL 2953 is used as the seed strain. Culturing is carried out in the same manner as described in Example 2. In such manner, 60 g of white powder is obtained as described in the step B of Example 1. As a result of paper chromatography, this powder is determined to contain each of the components of XK-62-2, gentamicin $C_1$, gentamicin $C_2$ and gentamicin $C_{1a}$. Each of these components is isolated in the free base form from the powder in the same manner as described in Example 2. The results are as follows:

| Component | Activity (unit/mg) | Yield (g) |
|---|---|---|
| gentamicin $C_1$ | 821 | 21 |
| XK-62-2 | 925 | 2 |
| gentamicin $C_2$ | 880 | 15 |
| gentamicin $C_{1a}$ | 850 | 7 |

EXAMPLE 7

In this example, *Micromonospora echinospora* ATCC 15837, NRRL 2985 *Micromonospora echinospora* var. *ferruginea* ATCC 15836, NRRL 2995, and *Micromonospora echinospora* var. *pallida* ATCC 15838, NRRL 2996 are used as seed strains. Culturing is carried out in the same manner as described in Example 2 to obtain a white powder comprising a mixture of the components from each of the culture liquors in the same manner as described in the step B of Example 1. Each of the components is then isolated in the free base form in the same manner as described in Example 2.

The activity and yield of each of the fractions thus isolated is as follows:

| | *Micromonospora echinospora* ATCC 15837 NRRL 2985 | | *Micromonospora echinospora* var. *ferruginea* NRRL 2995 | | *Micromonospora echinospora* var. *pallida* NRRL 2996 | |
|---|---|---|---|---|---|---|
| | activity (unit/mg) | yield (g) | activity (unit/mg) | yield (g) | activity (unit/mg) | yield (g) |
| Gentamicin $C_1$ | 906 | 15 | 830 | 13 | 940 | 18 |
| XK-62-2 | 898 | 3 | 912 | 1.5 | 925 | 2.5 |
| Gentamicin $C_2$ | 845 | 12 | 853 | 8 | 859 | 7.5 |
| Gentamicin $C_{1a}$ | 880 | 9 | 920 | 5.8 | 890 | 11 |

What is claimed is:

1. A process for the production of the antibiotic XK-62-2 which comprises; culturing a microorganism belonging to the species *Micromonospora sagamiensis*, which is capable of producing XK-62-2, in a nutrient medium until substantial antibacterial activity is detected in the culture liquor; and thereafter isolating said antibiotic therefrom.

2. A process according to claim 1 wherein said microorganism is *Micromonospora sagamiensis* ATCC 21826.

3. A process according to claim 1 wherein said microorganism is *Micromonospora sagamiensis* var. *flava* ATCC 21827.

4. A process according to claim 1 wherein said microorganism is *Micromonospora sagamiensis* var. *nonreducans* ATCC 21803.

5. A process according to claim 1 wherein said microorganism is *Micromonospora sagamiensis* var. *nonreducans* ATCC 21949.

6. A process according to claim 1 which includes the additional step of extracting the antibiotic from the microbial cells before said isolating step.

7. A process according to claim 1 wherein said culturing is carried out at a temperature of from 25° C to 42° C and at about neutral pH.

8. A process for the production of the antibiotic XK-62-2, which comprises; culturing an XK-62-2 producing microorganism selected from the group consisting of

*Micromonospora sagamiensis* ATCC 21826, *Micromonospora sagmiensis* var. *flava* ATCC 21827, *Micromonospora sagamiensis* var. *nonreducans* ATCC 21803 and ATCC 21949, *Micromonospora echinospora* ATCC 15837, *Micromonospora echinospora* var. *ferruginea* ATCC 15836, *Micromonospora echinospora* var. *pallida* ATCC 15838 and *Micromonospora purpurea* ATCC 15835 in a nutrient medium; accumulating XK-62-2 in said medium; and isolating the antibiotic XK-62-2 therefrom.

9. A process according to claim 8 wherein said culturing step is carried out at a temperature from 25° C to 42° C and at about neutral pH.

10. A process for the production of the antitiotics gentamicin $C_1$, gentamicin $C_2$ and gentamicin $C_{1a}$ which comprises culturing a microorganism belonging to the species *Micromonospora sagamiensis* which is capable of producing said antibiotics in a nutrient medium until substantial antibacterial activity is detected in the culture liquor; and thereafter isolating at least one of said antibiotics therefrom.

11. A process according to claim 10 wherein said microorganism is selected from the group consisting of *Micromonospora sagamiensis* ATCC 21826, *Micromonospora sagamiensis* var. *flava* ATCC 21827 and *Micromonospora sagamiensis* var. *nonreducans* ATCC 21803.

12. A process according to claim 10 wherein said culturing step is carried out at a temperature from 25° C to 42° C and at about neutral pH.

* * * * *